United States Patent [19]
Sohn

[11] Patent Number: 5,549,555
[45] Date of Patent: Aug. 27, 1996

[54] BALLOON CATHETER

[75] Inventor: Ze'ev Sohn, Modiin, Israel

[73] Assignee: Influence, Inc., Orangeburg, N.Y.

[21] Appl. No.: 392,137

[22] Filed: Feb. 22, 1995

[51] Int. Cl.$^6$ .................................................. A61M 29/00
[52] U.S. Cl. ............................................ 604/101; 604/104
[58] Field of Search ................................ 604/96, 97, 98, 604/99, 101, 103, 104, 264, 280, 284

[56] References Cited

U.S. PATENT DOCUMENTS

| | | |
|---|---|---|
| 3,734,083 | 5/1973 | Kolin ........................................ 604/104 |
| 4,581,017 | 4/1986 | Sahota . |
| 4,592,340 | 6/1986 | Boyles . |
| 4,601,713 | 7/1986 | Fuqua . |
| 5,344,402 | 9/1994 | Crocker . |
| 5,383,856 | 1/1995 | Bersin ..................................... 604/103 X |

Primary Examiner—Corrine M. McDermott
Assistant Examiner—N. Kent Gring
Attorney, Agent, or Firm—Levisohn, Lerner, Berger & Langsam

[57] ABSTRACT

A balloon catheter includes a flexible tubular body having a distensible portion inflatable by a balloon. The tubular body is formed with a longitudinally-extending split at the distensible portion, and the balloon is disposed around the distensible portion with the opposite ends of the balloon secured to the two longitudinal edges of the tubular body along the split. The arrangement is such that inflating the balloon dilates the tubular body at the distensible portion, and also applies a tension force to the longitudinal edges of the tubular body at the split, opening the tubular body at the split to produce a flowpath of large cross-sectional area for the fluid through the distensible portion.

22 Claims, 8 Drawing Sheets

BALLOON CATHETER

FIELD AND BACKGROUND OF THE INVENTION

The present invention relates to balloon catheters such as are used for dilation and/or fluid-delivery purposes, and particularly to such catheters for dilating a stenosis or occlusion in a body duct while maintaining fluid flow through the duct. The invention is especially useful for treating a stenosis or occlusion in a blood flow passage, and is therefore described below with respect to such an application, but it will be appreciated that the invention could also be used in many other applications.

Balloon catheters are used at the present time for opening stenoses or occlusions in coronary arteries or in other parts of the vascular system. A widely used treatment is called percutaneous transluminal coronary angioplasty (PTCA), which makes use of a dilatation catheter having a distensible portion in the form of an inflatable balloon at the distal end of the catheter. The physician, using fluoroscopy, guides the catheter through the vascular system until the distensible portion is positioned across the stenosis. The balloon is then inflated by supplying fluid under pressure through an inflation lumen leading to the balloon, to open the artery and to reestablish acceptable blood flow.

A primary concern of PTCA is the temporary blockage of blood flow during balloon inflation. Various perfusion dilation catheters have been developed to provide a path for blood flow through the distensible portion of the catheter during the inflation of the balloon. Examples of such known catheters are described in U.S. Pat. Nos. 4,581,017, 4,790,315, 4,944,745, 4,592,340 and 5,344,402. One of the as yet unsolved problems in such catheters is simultaneously providing three critical features: (1) high blood flow rate with a low flow resistance when the balloon is inflated; (2) a small catheter profile when the balloon is deflated to facilitate its insertion into the blood vessel; and (3) simplicity of operation. Ideally, a low-profile perfusion catheter would achieve high blood perfusion rates without requiring the operator to perform any function in addition to the balloon inflation.

OBJECTS AND BRIEF SUMMARY OF THE INVENTION

An object of the present invention is to provide a balloon catheter having advantages in all three of the above respects, i.e., permitting high fluid through-flow at relatively low flow resistance when the balloon is inflated, and providing a small insertion profile when the balloon is deflated, without requiring additional operator actions.

Another object of the invention is to provide a balloon catheter of the foregoing type particularly useful for PTCA treatments.

According to the present invention, there is provided a balloon catheter, comprising a flexible tubular body having a distensible portion including an inflatable balloon. The tubular body is formed with a longitudinally-extending split at the distensible portion; and the balloon is disposed around the distensible portion of the tubular body with the opposite ends of the balloon secured to the two longitudinal edges of the tubular body along the split. The arrangement is such that inflation of the balloon dilates the tubular body at the distensible portion, and also applies a tension force to the longitudinal edges of the tubular body at the split, opening the tubular body at the split to produce a flowpath of large cross-sectional area for the fluid through the distensible portion of the tubular body.

According to further features in the described preferred embodiments, the catheter further includes limiting means for limiting the opening of the catheter at the distensible portion of the catheter. In some described embodiments, the limiting means is or includes a flexible, non-stretchable membrane secured to the two longitudinal edges of the catheter along the split. In other described embodiments, the limiting means comprises a flexible, non-stretchable tubular membrane of a diameter to engage the outer surface of the distensible portion of the tubular body, when inflated, to thereby limit the opening of such distensible portion.

According to some described embodiments, the tubular body includes, at the distensible portion, at least one initially tubular section formed with the longitudinally-extending split, the balloon being disposed around the initially tubular section with the opposite ends of the balloon secured to the two longitudinal edges of the tubular body along the split.

A preferred embodiment is described below wherein the tubular body includes two initially tubular sections and joined by a longitudinally-extending juncture formed with the split, and a membrane secured to the two longitudinal edges of the juncture at the split. The tubular body can be formed with the two initially tubular sections only at the distensible portion of the tubular body. When the distensible portion is inflated, these two initially tubular sections are opened into a single tubular section for the fluid flow therethrough. Preferably, the two tubular sections and the limiting means (e.g., a membrane joining the longitudinal edges of the sections along the split, or a tubular membrane enclosing the distensible portion of the catheter) is designed such that the catheter assumes a substantially circular cross-section in its open condition.

In some embodiments, the catheter proximal to the distensible section includes a tubular body with at least two lumens. One lumen may be used for a guide wire, and one lumen may be provided for balloon inflation. The balloon inflation lumen terminates at the balloon. The guide wire lumen is generally aligned with one of the distensible tube sections. The distensible tube section may then be used for the guide wire.

In one preferred embodiment which has two initially tubular sections at the distensible portion of the tubular body, the tubular body can be formed for its complete length with the two tubular sections. One tubular section may be used for the guide wire, and one tubular section may be used for balloon inflation.

Distal to the distensible balloon, the catheter may have at least one lumen for the guide wire.

For some applications particularly where larger-diameter ducts are involved, it may be desirable to provide the catheter with more than two initially tubular sections. Embodiments are described below including a clover-leaf arrangement, and also a side-by-side arrangement, in both of which the catheter is provided with three (or more) initially tubular sections.

Each of the balloons may be a separate balloon; alternatively, all the balloons may be constituted of a single balloon divided into sections.

Another embodiment is described below in which the tubular body includes, at the distensible portion, a wound, helical section of the tubular body. The helical section has an outer edge joined to its inner edge by the opposite ends of the balloon also wound with the helical section, such that inflation of the balloon applies a tension force to the inner and outer edges of the helical section to open the helical section into a tubular configuration of relatively large diameter. In that described embodiment, the limiting means is in the form of a flexible, non-stretchable, tubular membrane of a diameter to engage the outer surface of the balloons when inflated, and thereby to limit the opening of the distensible portion of the tubular body.

Another feature of the preferred embodiments is that the split or splits may extend longitudinally beyond the balloons. When the balloons are inflated, the splits proximal and distal to the balloons are widened. This provides increased blood flow into and out of the tubular sections that pass through the balloons.

As will be described more particularly below, balloon catheters constructed in accordance with the foregoing features provide high fluid through-flow with low fluid flow resistance when inflated, and also provide a relatively small insertion profile when deflated.

As indicated above, the invention is particularly useful in PTCA treatments, and therefore the catheter and balloon are dimensioned for insertion into a blood vessel for dilating a stenosis or occlusion therein.

Further features and advantages of the invention will be apparent from the description below.

BRIEF DESCRIPTION OF THE DRAWINGS

The invention is herein described, by way of example only, with reference to the accompanying drawings, wherein:

FIGS. 3a and 3b diagrammatically illustrate a cross-section of the distensible portion of a catheter having two-lumen construction in accordance with the invention, during the non-inflated and fully-inflated conditions of the distensible portion; whereas

DESCRIPTION OF PREFERRED EMBODIMENTS

Figure 1:
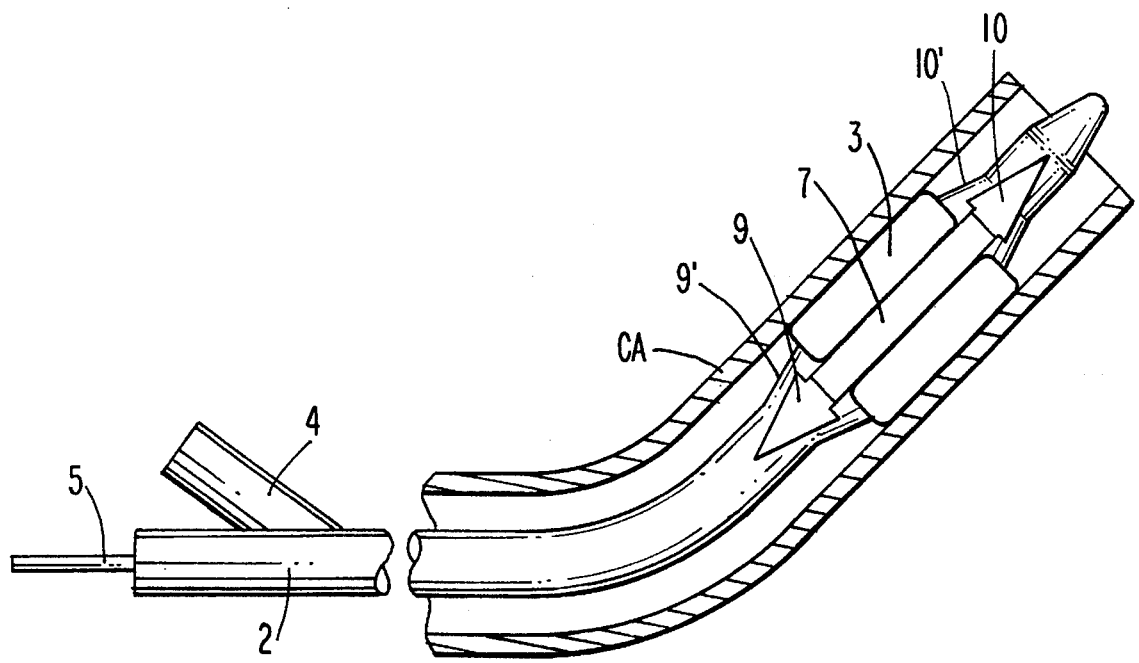
FIG. 1 illustrates one form of balloon catheter constructed in accordance with the present invention for insertion into a blood flow passage in order to dilate the stenosis or occlusion therein according to the abovedescribed PTCA treatment.

The catheter illustrated in FIG. 1 is designed for dilating a stenosis or occlusion in a blood flow passageway, such as a coronary artery CA, while maintaining blood flow through the artery. The illustrated catheter 2 includes an elongate flexible tubular body having an inflatable balloon 3 at its distal end. Balloon 3 is inflated by a pressurized fluid applied through an inlet port 4 at the proximal end of the catheter. The catheter 2 is guided through the coronary artery CA by a guide wire 5 also applied via the proximal end of the catheter.

Figure 2A:
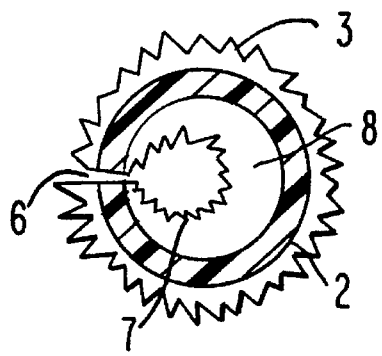
FIGS. 2a, 2b and 2c diagrammatically illustrate a cross-section of the distensible portion of the catheter of FIG. 1 during its non-inflated, partially-inflated, and fully-inflated conditions, respectively; whereas FIGS. 2d and 2e diagrammatically illustrate a longitudinal section of the distensible portion of the catheter in its non-expanded and fully-expanded conditions, respectively.

At the distensible portion of the catheter, namely the portion occupied by balloon 3, the catheter 2 is formed with a split extending longitudinally of the catheter. As shown particularly in FIGS. 2a, 2b, and 2d, balloon 3 is applied around the catheter 2 at the distensible portion with the opposite ends of the balloon secured to the two longitudinal edges of the catheter along the split 6. A flexible, non-stretchable membrane 7 is secured to the two longitudinal edges of the catheter 2 along split 6.

In the non-inflated condition of balloon 3 (FIGS. 2a, 2d), catheter 2 defines a tubular lumen 8 within it in which the membrane 7 is located in a folded or free (untaut) condition. For illustrative purposes the balloon is shown removed from the catheter 2. In practice, as is common in balloon catheters, the balloon in the non-inflated state is pressed flush against the catheter body.

Figure 2B:
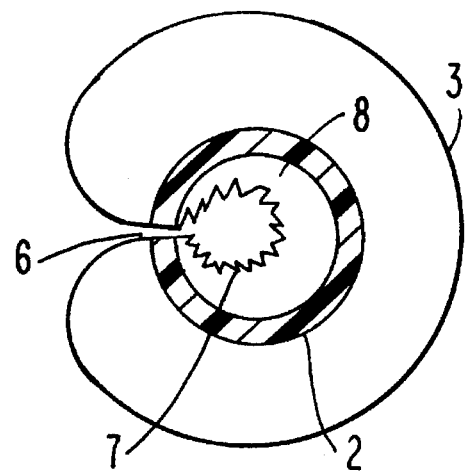
Figure 2C:
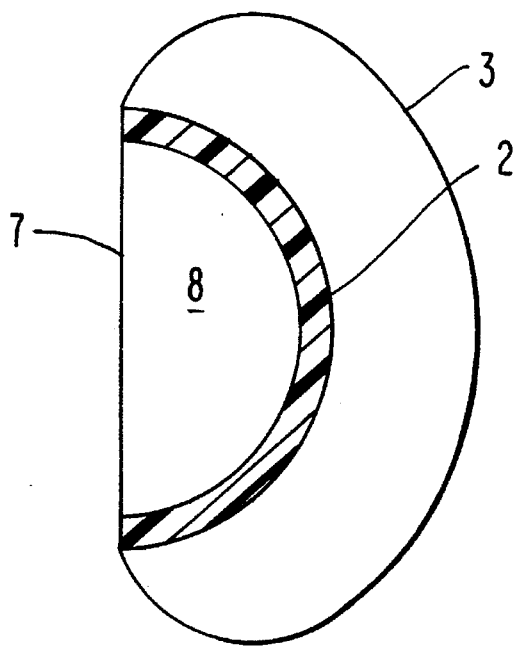
Figure 2D:
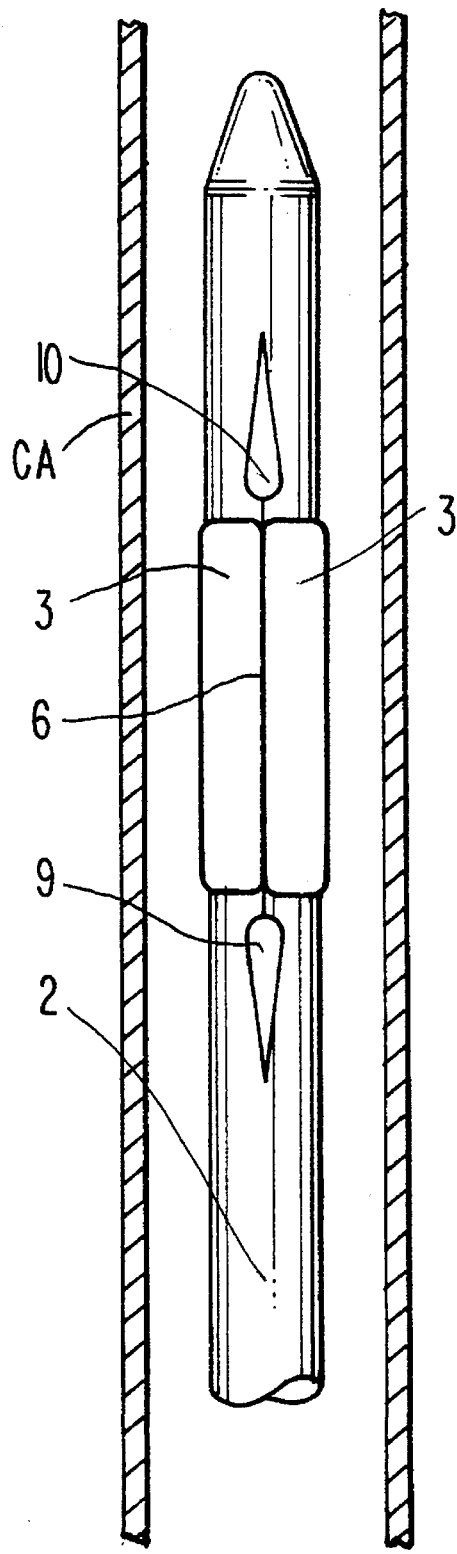
Figure 2E:
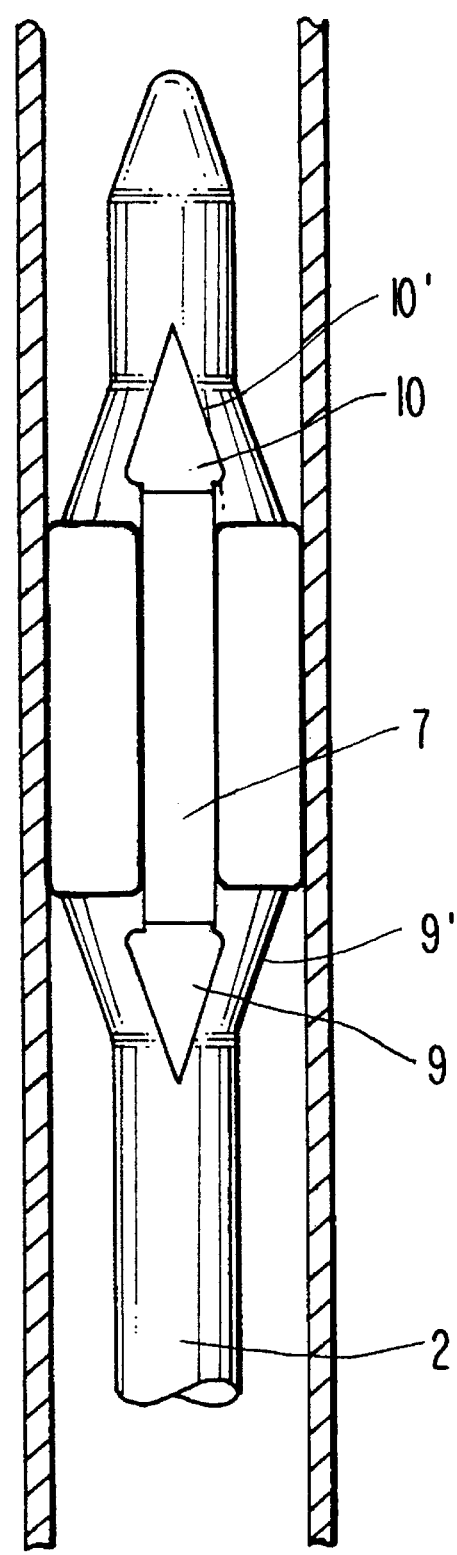

As balloon 3 is inflated by the application of pressurized fluid thereto via fluid entry port 4, the catheter is expanded or dilated as shown in FIGS. 2b, 2c and 2e. During this inflation of the balloon, the balloon applies a tension force to the longitudinal edges of the catheter 2 to open the catheter from the circular configuration illustrated in FIGS. 2a and 2b, to the semi-circular configuration illustrated in FIG. 2c. The opening of the catheter is limited by membrane 7 which becomes taut and thereby prevents the further spreading apart of the split ends of the catheter 2.

It will be seen that during this opening of the catheter 2 by the inflation of balloon 3, the lumen 8 defined by the catheter increases in cross-sectional area, and thus provides a flowpath of increased cross-sectional area for the blood flow through the distensible portion of the catheter.

Catheter 2 is formed with an inlet opening 9 at the proximal side of the distensible portion defined by balloon 3, and an exit opening 10 at the distal side of the distensible portion. The inlet opening 9 and the exit opening 10 are contiguous with the split 6. As shown in FIGS. 1 and 2e, when balloon 3 becomes inflated, the juncture, shown at 9', at the proximal side of the distensible portion expands into a conical configuration with the inlet opening 9 therein also increasing in size. Similarly, the juncture 10' at the distal side of the distensible portion also expands into a conical configuration, with the exit opening 10 therein also increasing in size.

It will thus be seen that when balloon 3 has been inflated for dilating a stenosis or occlusion, proximal opening 9, lumen 8, and distal opening 10, provide a flowpath of relatively large cross-sectional area for maintaining high through-flow and low flow resistance of the blood flow through the distensible portion of the catheter.

However, a disadvantage of the construction illustrated in FIGS. 2a–2e is that the large cross-sectional area lumen 8 produced by the inflation of balloon 3 is of semi-circular cross-section. Such a shape is much less efficient with respect to pressure distribution than a circular cross-sectional lumen. The remaining drawings illustrate catheter constructions for producing circular cross-section lumens at the distensible portion when dilated.

Thus, as shown in FIGS. 3a–3d, the catheter includes two initially tubular sections 12a, 12b at the distensible portion joined together at a longitudinally-extending juncture along two longitudinal edges 12c and 12d. In this case, the split (corresponding to split 6 in FIGS. 2a–2c) is formed in the juncture as shown at 16. A balloon 13a, 13b is applied around each tubular catheter section 12a, 12b, and is secured at its opposite ends to the two longitudinal edges 12c and 12d of the respective catheter section at split 16. A flexible, non-stretchable membrane 17 is secured to the two longitudinal edges 12c and 12d of the juncture at the split 16.

Figure 3A:
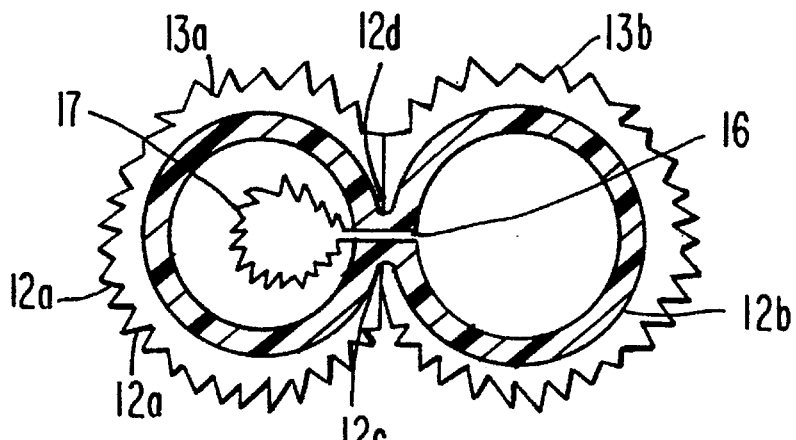
Figure 3B:
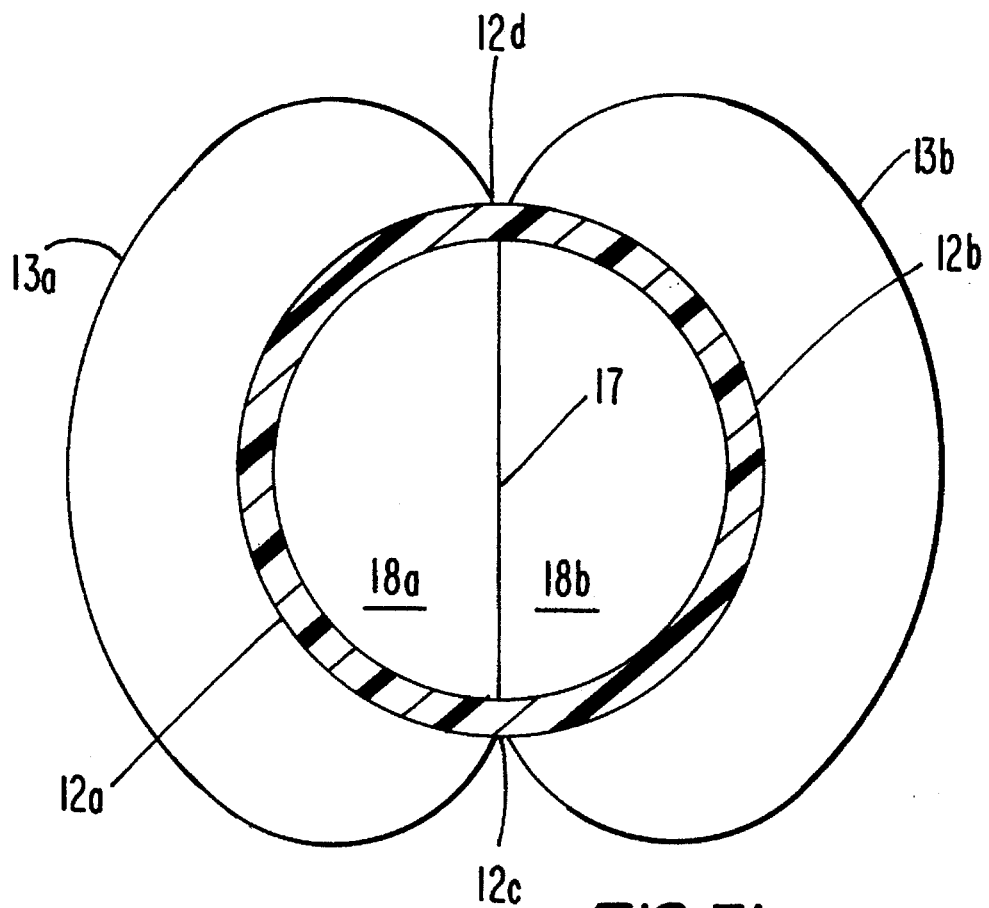

It will thus be seen that when the two balloons 13a, 13b are inflated (by the application of a pressurized fluid via the fluid inflation port 4, FIG. 1), the two balloons 13a, 13b expand and apply a tension force opening the two initially tubular sections 12a, 12b until limited by the membrane 17, as shown in FIG. 3b. The inflation of the two balloons thus not only dilates the distensible portion of the catheter, but also produces two lumens 18a, 18b of enlarged, semicircular cross-sectional area for the blood flow through the distensible portion. The two lumens 18a, 18b together define a single lumen of near circular cross-section. This cross-section is optimal for resisting the pressure exerted on the lumen. The two balloons together also form a near circular cross-section, thereby providing a better pressure distribution.

FIGS. 3a–3d illustrate such limiting means being in the form of a single membrane 17. It will be appreciated, however, that other limiting means could be used, for example two membranes, or flexible, non-stretchable filaments rather than a continuous membrane. The limiting means illustrated in FIGS. 6a and 6b, as to be described below, could also be used, namely a flexible, non-stretchable, tubular membrane having a diameter to engage the outer surface of the distensible portion of the catheter, when inflated, and thereby to limit the degree of expansion of that portion.

The catheter illustrated in FIGS. 3a–3d may be formed with the two initially tubular sections 12a, 12b for the complete length of the catheter, or only at the distensible portion of the catheter, i.e., the portion of the catheter occupied by the balloons 13a, 13b.

Figure 3C:
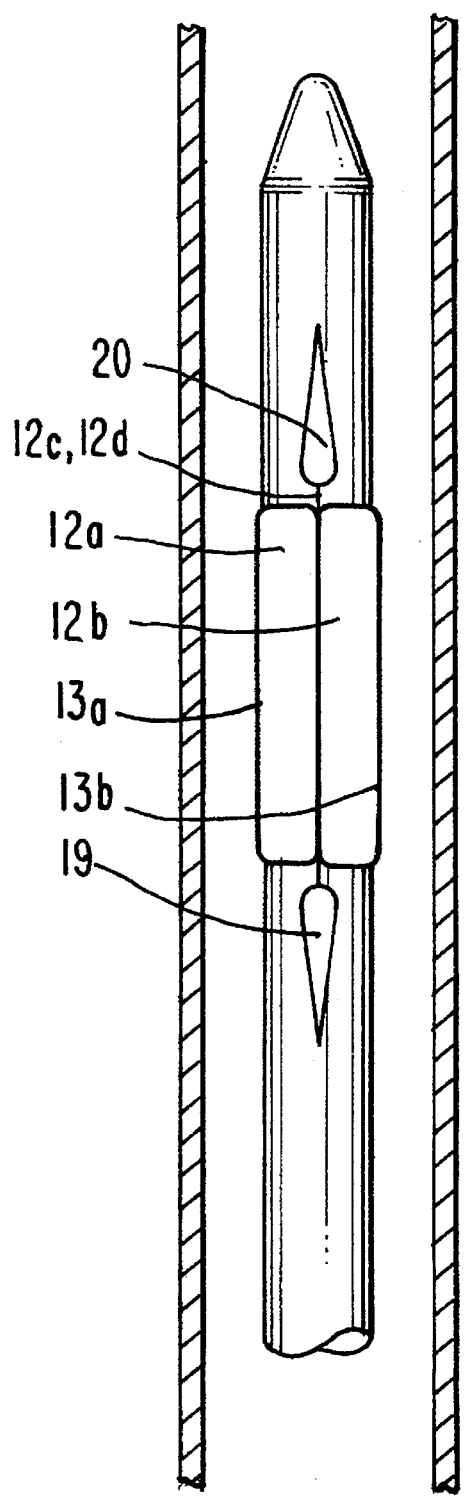
FIGS. 3c and 3d illustrate a longitudinal section of the catheter in its non-inflated and fully-inflated conditions, respectively.
Figure 3D:
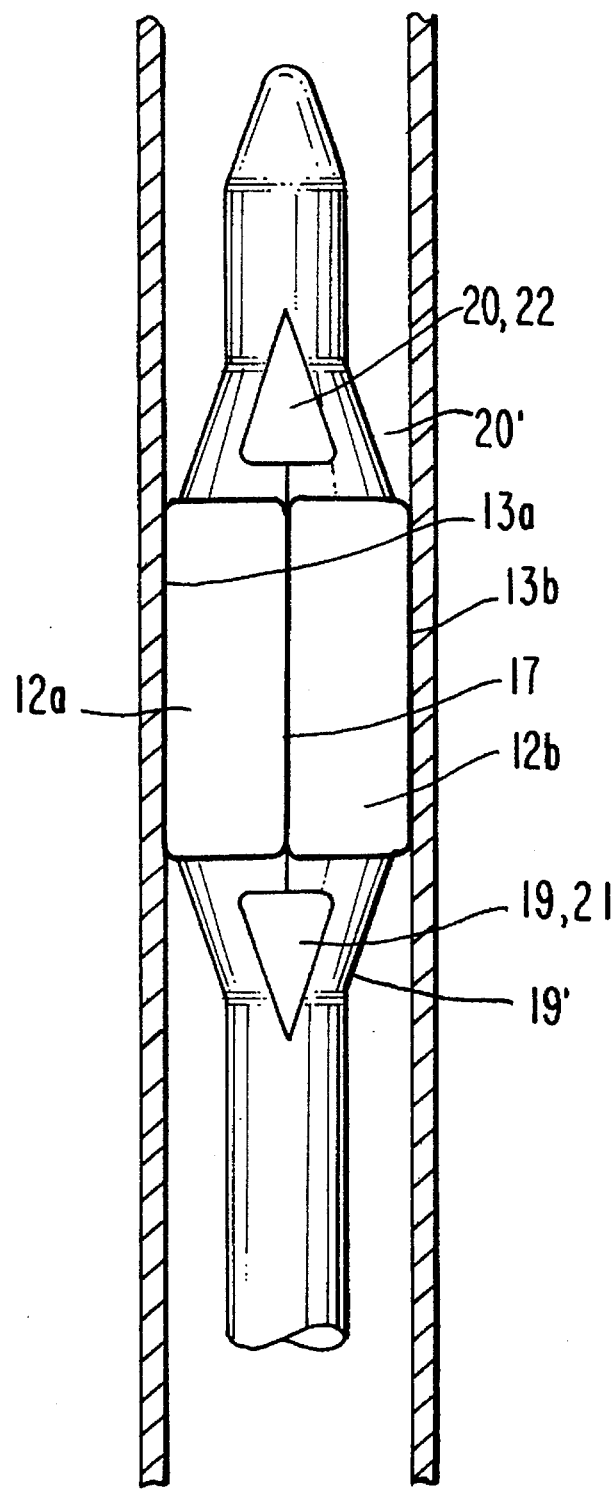

FIGS. 3c and 3d illustrate the additional advantage described above of this construction, in that the proximal juncture 19' and the distal juncture 20' of the distensible portion enlarge into conical configuration upon the inflation of the distensible portion, thereby also enlarging their inlet openings 19 and 21 and outlet openings 20 and 22. Openings 19 and 21 are contiguous with longitudinal edge 12c, and openings 20 and 22 are contiguous with longitudinal edge 12d. This enlargement of the inlet and outlet openings further decreases the resistance of the blood flow through the distensible portion of the lumen during its dilation.

FIGS. 4a, 4b and 5a, 5b illustrate catheters in which the tubular portion is formed with three (or more) initially tubular sections which, when inflated, are expanded into a single large lumen for the blood flow.

Figure 4A:
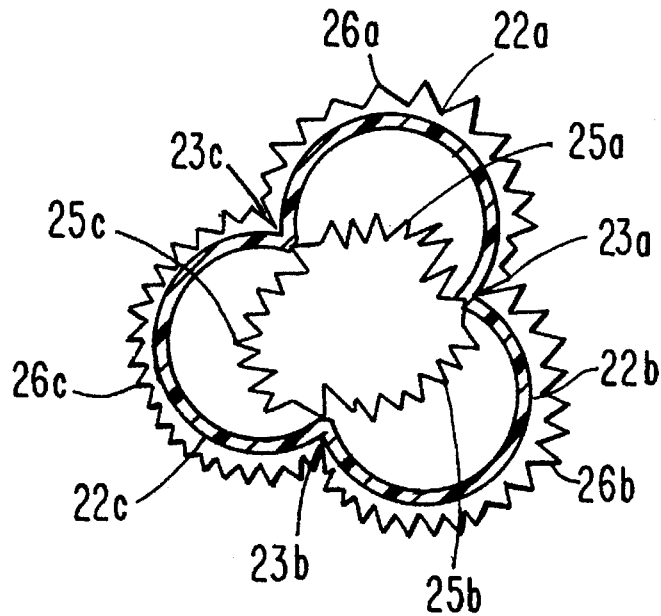
FIGS. 4a and 4b are views corresponding to FIGS. 3a and 3b of a catheter including three lumens arranged in a clover-leaf array.
Figure 4B:
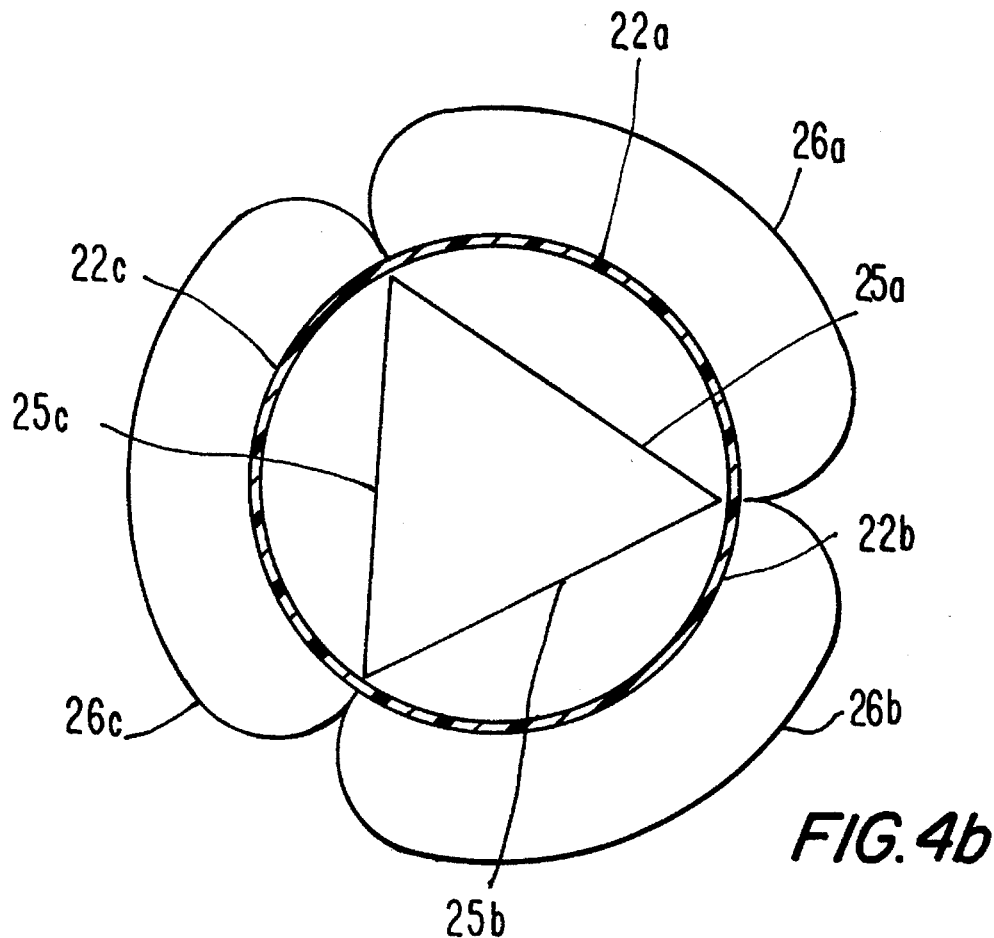

Thus, in FIGS. 4a and 4b, the distensible portion of the catheter (or alternatively, of the complete catheter) is formed with three initially tubular sections 22a, 22b, 22c, in a clover-leaf array; that is, they are joined together along three longitudinally-extending junctures 23a, 23b, 23c at the center region of the clover-leaf array. The three junctures 23a–23c thus define longitudinally-extending splits in the non-inflatable condition of the catheter. A flexible, non-stretchable membrane 25a, 25b, 25c is secured across each of the initially tubular sections 22a–22c between their respective longitudinally-extending junctures 23a–23c.

Inflatable balloons 26a, 26b and 26c are applied around each of the tubular sections 22a–22c and are secured at their opposite ends to their longitudinal edges of the respective junctures.

FIG. 4b illustrates the fully-inflated condition of the catheter of FIG. 4a, wherein it will be seen that the three initially-tubular sections 22a–22c are inflated until their respective membranes 25a–25c become taut, at which time the three tubular sections define a lumen of enlarged cylindrical configuration.

Figure 5A:
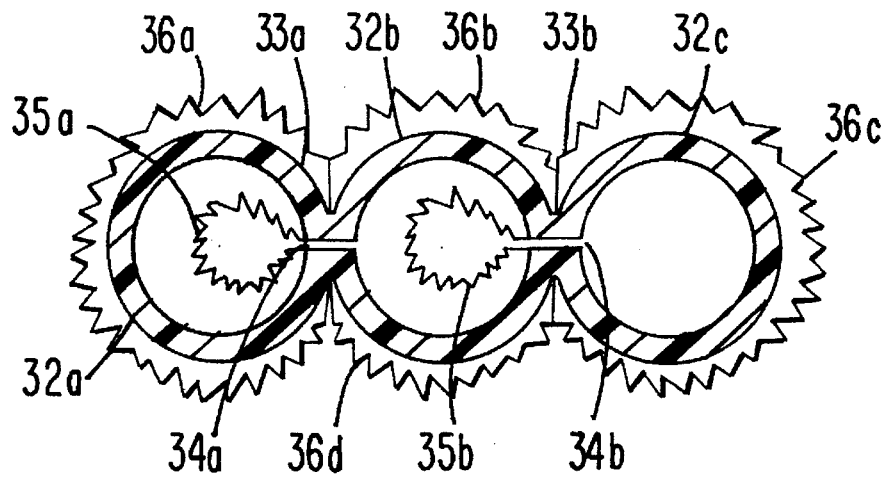
FIGS. 5a and 5b are views corresponding to FIGS. 3a and 3b of a catheter including three lumens arranged in a side-by-side array.
Figure 5B:
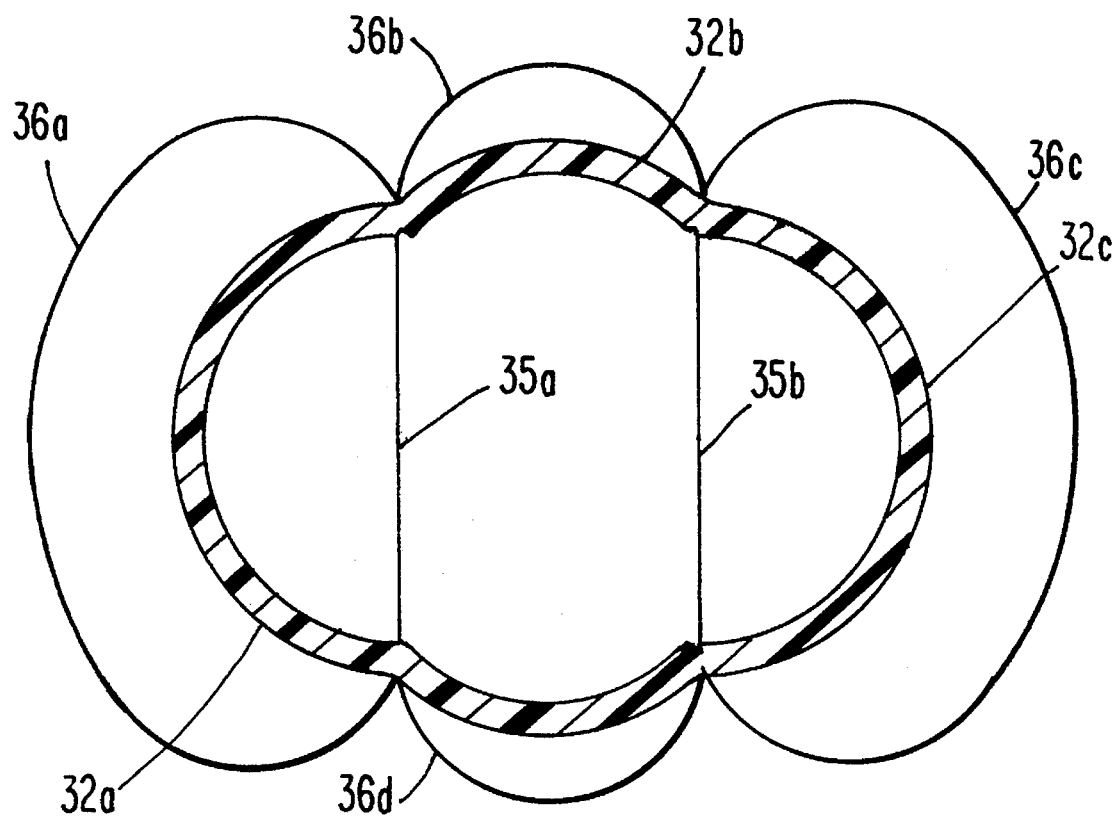

FIGS. 5a and 5b illustrate a catheter formed with four initially tubular sections 32a–32d. In this case they are arranged in a side-by-side array joined together along two longitudinally-extending junctures 33a, 33b, with each juncture formed with a longitudinally-extending split 34a, 34b. A flexible, non-stretchable membrane 35a, 35b is secured to the two longitudinal edges of each of the junctures along their respective split.

Inflatable balloons are applied around each of the four initially tubular sections and are secured at the opposite ends of the balloon to the longitudinal edges of the respective juncture at the split. Thus, a balloon 36a is applied around the outer catheter section 32a, and a second balloon 36c is applied around the outer catheter sections 32c. However, a smaller balloon 36b is applied around section 32b, and another smaller balloon 36d is applied around the opposite side of the middle catheter section 32d.

FIG. 5b illustrates the distensible portion of the catheter of FIG. 5a when all the balloons are inflated, wherein it will be seen that they produce a flow passage of large circular cross-sectional area through the distensible portion of the catheter.

It will be appreciated that in the three-section constructions illustrated in FIGS. 4a, 4b, and 5a, 5b, the proximal and distal junctures (not shown) of the distensible portion of the catheter also become enlarged into a conical configuration upon the inflation of the distensible portion, and that the inlet and outlet openings formed in these junctures also become enlarged, in the same manner as illustrated in FIGS. 2d and 2e for the single-section configuration and in FIGS. 3c and 3d for the two-lumen configuration. The structures illustrated in FIGS. 4a, 4b, and 5a, 5b thus also provide flowpaths of high through-flow and low resistance when the catheter is inflated, and a small insertion profile when the catheter is deflated to facilitate insertion.

It will also be appreciated that, for some applications, the catheter could include even more than three sections where large ducts or passages are to be dilated while maintaining fluid flow through the duct or passage. Thus, a catheter construction including four or more sections could be provided as described above, either according to the clover-leaf array as shown in FIGS. 4a and 4b, or according to the side-by-side array as shown in FIGS. 5a and 5b.

Figure 6A:
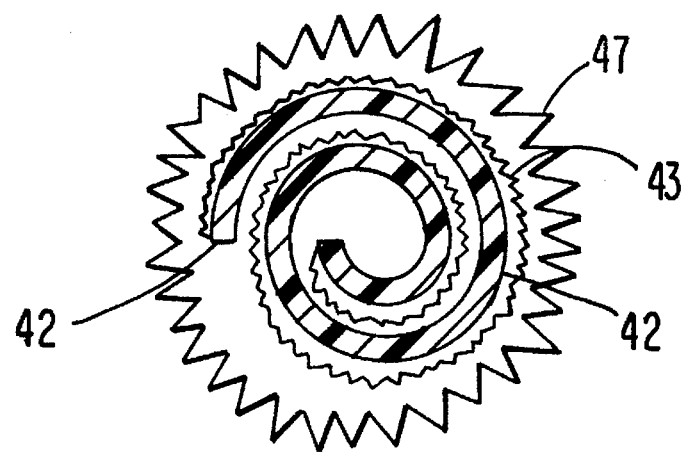
FIGS. 6a and 6b diagrammatically illustrate the distensible portion of another construction of catheter in accordance with the present invention during the non-expanded and fully-expanded condition of the distensible portion.
Figure 6B:
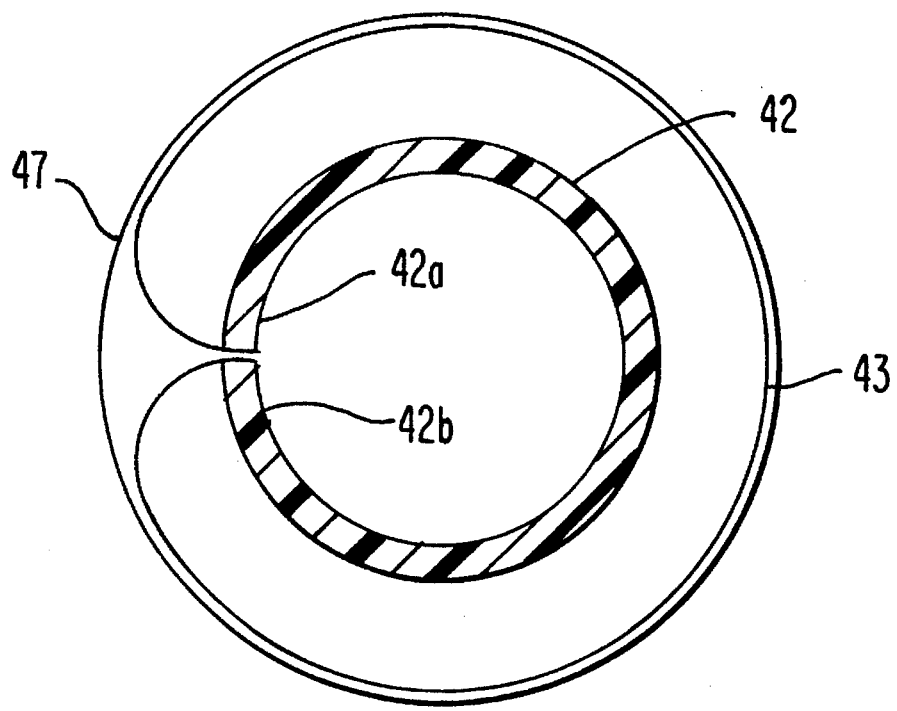

FIGS. 6a and 6b illustrate the distensible portion of a further catheter construction that may be used. In this case, the catheter wall 42, at the distensible portion of the assembly occupied by the balloon 43, is split longitudinally of the catheter and is wound into a helical configuration, with the deflated balloon 43 being wound with the catheter wall. Thus, one end of balloon 43 is secured to the outer edge 42a of the wound catheter wall, and the opposite end of the balloon is secured to the inner edge 42b of the wound catheter wall. The limiting means in this construction is in the form of a tubular membrane 47 enclosing the helically-configured catheter wall and balloon. Tubular member 47 is of a flexible, non-stretchable material, and has a diameter corresponding to the outer diameter of the distensible portion of the catheter when fully dilated, to thereby limit the opening of the catheter during the inflation of the balloon.

FIG. 6a illustrates the condition of the distensible portion of the catheter when the balloon 43 is deflated; and FIG. 6b illustrates its condition when the balloon is inflated. For illustrative purposes, the tubular member 47 in FIG. 6a is shown removed from the catheter. In practice, the tubular member 47 is pressed flat against the outer rim of the balloon and catheter spiral. Tubular member 47 may be joined at several points or along a line with the catheter in order to fix its location.

As shown in FIG. 6b, this construction also provides a flowpath of large circular cross-section at the time the balloon is inflated to dilate a stenosis or occlusion, thereby maintaining low-resistance fluid flow through the dilated portion of the catheter, while at the same time providing the catheter with a small deflated profile to facilitate insertion of the catheter in its deflated condition. Also in this construction, the junctures of the distensible portion of the cathether with the proximal and distal sides would also be expanded into a conical configuration, and their respective inlet and outlet openings would also be enlarged upon the expansion of the extensible portion, as described above with respect to the catheter of FIGS. 2d and 2e, and the catheter of FIGS. 3c and 3d.

While the invention has been described with respect to several preferred embodiments, it will be appreciated that these are set forth merely for purposes of example, and that many other variations, modifications and applications of the invention may be made.

I claim:

1. A balloon catheter, comprising:
    a flexible tubular body having a distensible portion, said distensible portion being a section of said balloon catheter comprising an inflatable balloon;
    said tubular body being formed with a longitudinally-extending split at said distensible portion, said longitudinally-extending split having two longitudinally-extending edges, said longitudinally-extending edges being a first edge and a second edge;
    said balloon being attached to said distensible portion of said tubular body with a first portion of said balloon secured to said first edge and a second portion of said balloon secured to said second edge, such that inflation of said balloon applies a tension force to said first and second edges of said tubular body, pulling said first edge and said second edge apart and opening said distensible portion at said longitudinally-extending split to produce a flowpath of larger cross-sectional area within said distensible portion for the passage of fluid through said distensible portion of said tubular body.

2. The catheter according to claim 1, further including limiting means for limiting the opening of said tubular body at said distensible portion during inflation of said balloon.

3. The catheter according to claim 2, wherein said limiting means comprises a membrane secured to said longitudinally-extending edges of said tubular body along said longitudinally-extending split, a first portion of said membrane attached to said first edge, and second portion of said membrane attached to said second edge.

4. The catheter according to claim 2, wherein said limiting means comprises a flexible, non-stretchable, tubular membrane of a diameter to engage the outer surface of said balloon when inflated, to thereby limit the opening of said distensible portion of the tubular body.

5. The catheter according to claim 1, wherein said tubular body includes, at said distensible portion, at least one initially tubular section formed with said longitudinally-extending split; said balloon being disposed around said initially tubular section with the opposite ends of the balloon secured to said longitudinally-extending edges of the tubular body along said split.

6. The catheter according to claim 1, wherein said tubular body includes, at said distensible portion, two initially tubular sections joined together along a longitudinally-extending juncture, said juncture being formed with said longitudinally-extending split; said catheter including two balloons, one around each of said two sections and secured at opposite ends to said longitudinally-extending edges of the respective section at the said longitudinally-extending split, such that inflation of the two balloons applies a tension force to said longitudinally-extending edges of said two initially tubular sections to cause them to open into a single tubular configuration of a relatively large diameter at said distensible portion of said tubular body.

7. The catheter according to claim 6, further including limiting means for limiting the opening of said two initially tubular sections upon the inflation of said balloons.

8. The catheter according to claim 7, wherein said limiting means includes a flexible, non-stretchable membrane secured to said longitudinally extending edges of said juncture at said split.

9. The catheter according to claim 6, wherein said tubular body includes, at said distensible portion, at least three initially tubular sections joined together along longitudinally-extending junctures each formed with said longitudinally-extending split, there being a balloon section disposed around each of said initially tubular sections with the opposite ends of each balloon section secured to said longitudinally-extending edges of each of said initially tubular sections along their respective splits.

10. The catheter according to claim 9, wherein said at least three initially tubular sections are formed according to a clover-leaf array with their longitudinally-extending junctures at the center of the clover-leaf array.

11. The catheter according to claim 9, wherein said at least three initially tubular sections are formed according to a side-by-side array with a longitudinally-extending juncture joining each of the two outer tubular sections with the middle tubular section.

12. The catheter according to claim 9, further including limiting means for limiting the opening of said tubular body at said distensible portion during inflation of said balloon sections.

13. The catheter according to claim 12, wherein said limiting means comprises a membrane secured to said longitudinally-extending edges of each of the initially tubular sections at their respective splits.

14. The catheter according to claim 12, wherein said limiting means comprises a flexible, non-stretchable, tubular membrane of a diameter to engage the outer surface of said balloon sections when inflated, and thereby to limit the opening of said distensible portion.

15. The catheter according to claim 1, wherein said tubular body includes, at said distensible portion, a wound, helical section of the tubular body, said helical section having a first outer edge joined to its second inner edge by the opposite ends of said balloon also wound with said helical section, such that inflation of the balloon applies a tension force to the inner and outer edges of said helical section to open said helical section into a tubular configuration of relatively large diameter.

16. The catheter according to claim 15, further including limiting means in the form of a flexible, non-stretchable tubular membrane enclosing said wound helical section and of a diameter to engage the outer surface of said balloon, when inflated, to thereby limit the opening of said distensible portion.

17. The catheter according to claim 1, wherein said distensible portion of the tubular body is joined to the proximal end of the tubular body by a juncture which becomes conical upon the dilation of the distensible portion, said juncture being formed with an inlet opening for the fluid to flow into the interior of the distensible portion, which inlet opening also increases in size with the dilation of the distensible portion.

18. The catheter according to claim 17, wherein said distensible portion is joined to the distal end of the tubular body by another juncture which also becomes conical upon the dilation of the distensible portion, said latter juncture being formed with an outlet opening for the flow of the fluid from the interior of the distensible portion, which outlet opening also increases in size with the dilation of the distensible portion.

19. The catheter according to claim 1, wherein said tubular body includes a guide wire for guiding the insertion of the tubular body through a body duct.

20. The catheter according to claim 1, wherein said tubular body and balloon are dimensioned for insertion into a blood vessel for dilating a stenosis.

21. A balloon catheter as claimed in claim 1, wherein said longitudinally-extending split extends beyond said balloon in a first direction.

22. A balloon catheter as claimed in claim 21, wherein said longitudinally-extending split extends beyond said balloon in a second direction.

* * * * *